(12) United States Patent
Gray et al.

(10) Patent No.: US 11,951,221 B2
(45) Date of Patent: Apr. 9, 2024

(54) SILVER AND TITANIUM DIOXIDE BASED OPTICALLY TRANSPARENT ANTIMICROBIAL COATINGS AND RELATED METHODS

(71) Applicant: Northwestern University, Evanston, IL (US)

(72) Inventors: Kimberly A. Gray, Evanston, IL (US); Yechan Won, Evanston, IL (US); Kevin Schwartzenberg, Chicago, IL (US)

(73) Assignee: Northwestern University, Evanston, IL (US)

( * ) Notice: Subject to any disclaimer, the term of this patent is extended or adjusted under 35 U.S.C. 154(b) by 830 days.

(21) Appl. No.: 17/043,169

(22) PCT Filed: Jun. 18, 2019

(86) PCT No.: PCT/US2019/037624
§ 371 (c)(1),
(2) Date: Sep. 29, 2020

(87) PCT Pub. No.: WO2019/246025
PCT Pub. Date: Dec. 26, 2019

(65) Prior Publication Data
US 2021/0015952 A1    Jan. 21, 2021

Related U.S. Application Data

(60) Provisional application No. 62/686,865, filed on Jun. 19, 2018.

(51) Int. Cl.
*A61L 2/10* (2006.01)
*A01N 59/00* (2006.01)
(Continued)

(52) U.S. Cl.
CPC ............... *A61L 2/10* (2013.01); *A01N 59/00* (2013.01); *A01N 59/16* (2013.01); *B01J 23/50* (2013.01);
(Continued)

(58) Field of Classification Search
CPC . A61L 2/088; A61L 2/10; A61L 2/232; A61L 2/238; A01N 59/00; A01N 59/16; B01J 23/50; B01J 35/004; B01J 35/006
See application file for complete search history.

(56) References Cited

U.S. PATENT DOCUMENTS 6,093,407 A    7/2000 Cummings et al.
7,560,409 B2   7/2009 Pitts, Jr. et al.
(Continued)

FOREIGN PATENT DOCUMENTS

| CN | 102628213 B | 12/2013 |
| CN | 107500558 A | 12/2017 |
| KR | 100752111 B1 | 8/2007 |

OTHER PUBLICATIONS

Awazu K et al., "A plasmonic photocatalyst consisting of silver nanoparticles embedded in titanium dioxide," *Journal of the American Chemical Society* (2008), vol. 130, pp. 1676-1680.
(Continued)

*Primary Examiner* — Timothy C Cleveland
(74) *Attorney, Agent, or Firm* — Bell & Manning, LLC

(57) ABSTRACT

Methods of reducing microbial attachment to a surface are provided, including methods comprising illuminating a surface comprising a substrate and a coating on the substrate with ultraviolet light, wherein the coating comprises anatase titanium dioxide nanoparticles functionalized with silver nanoparticles and is optically transparent to visible light; and exposing the illuminated surface to microbes. The coating exhibits a reduction in microbial attachment as compared to the coating absent the illumination.

18 Claims, 12 Drawing Sheets

(51) Int. Cl.
*A01N 59/16* (2006.01)
*B01J 23/50* (2006.01)
*B01J 35/00* (2006.01)

(52) U.S. Cl.
CPC ........... *B01J 35/004* (2013.01); *B01J 35/006* (2013.01); *A61L 2202/11* (2013.01); *A61L 2202/25* (2013.01)

(56) References Cited

U.S. PATENT DOCUMENTS

| | | | |
|---|---|---|---|
| 9,352,299 | B2 | 5/2016 | Kerrod et al. |
| 10,130,097 | B2 | 11/2018 | Meier et al. |
| 2012/0034435 | A1 | 2/2012 | Borrelli et al. |
| 2019/0337013 | A1* | 11/2019 | Dadheech .............. B05D 3/107 |

OTHER PUBLICATIONS

Sunada K, Watanabe T, Hashimoto K (2003) "Studies on photokilling of bacteria on TiO2 thin film," *Journal of Photochemistry and Photobiology A: Chemistry* (2003), vol. 156, pp. 227-233.

N Nino-Martinez et al., "Characterization of silver nanoparticles synthesized on titanium dioxide fine particles," *Nanotechnology* (2008), vol. 19, 065711 (8 pp).

Guifen Fu et al., "Anatase TiO2 Nanocomposites for Antimicrobial Coatings," *J. Phys. Chem. B* 2005, vol. 109, pp. 8889-8898.

Yen-Chi Chen et al., "Enhanced antimicrobial efficacy of thermal-reduced silver nanoparticles supported by titanium dioxide," *Colloids and Surfaces B: Biointerfaces* (2017), vol. 154, pp. 195-202.

S.A.H. Jalali et al., "The antibacterial properties of Ag/TiO2 nanoparticles embedded in silane sol-gel matrix," *Journal of the Taiwan Institute of Chemical Engineers* (2016), vol. 66, pp. 357-362.

X. H. Yang et al., "Synthesis of silver-titanium dioxide nanocomposites for antimicrobial applications," *J. Nanopart. Res.* (2014), vol. 16, pp. 2526 (13 pp).

Zhenyu Bo et al., "Size-Selective Synthesis and Stabilization of Small Silver Nanoparticles of TiO2 Partially Masked by SiO2," *Chemistry of Materials* (2015), vol. 27, pp. 1269-1277.

Yechan Won et al., "TiO2-based transparent coatings create self-cleaning surfaces," Chemosphere (2018), vol. 208, pp. 899-906.

The International Search Report and Written Opinion issued for International Patent Application No. PCT/US19/37624 dated Sep. 17, 2019, pp. 1-13.

C. Liu et al., "Mechanisms of the Enhanced Antibacterial Effect of Ag—TiO2 Coatings," Biofouling (2018), vol. 34, No. 2, pp. 190-199.

* cited by examiner

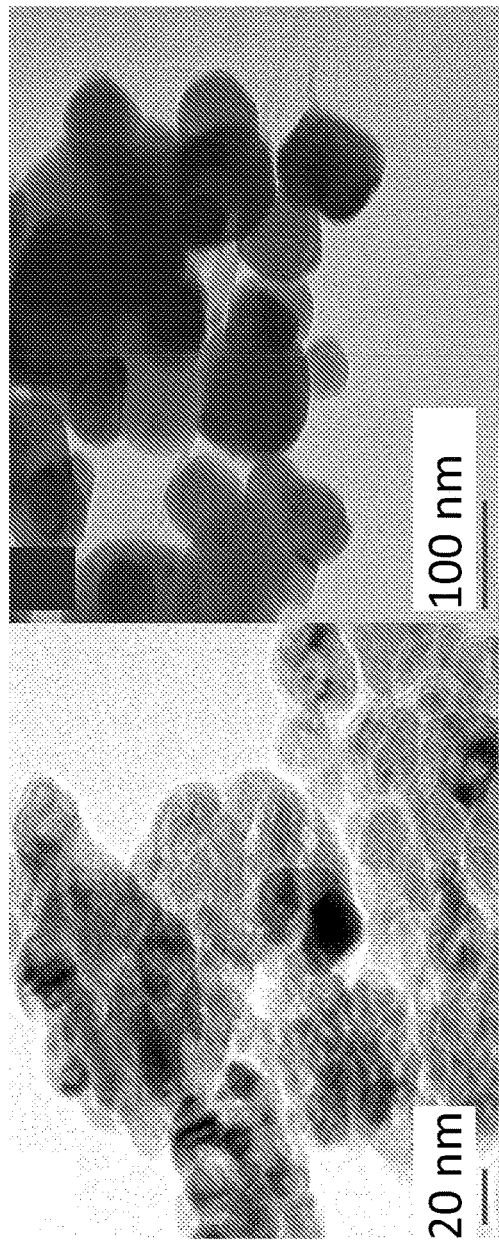
FIG. 1A  FIG. 1B  FIG. 1C  FIG. 1D

SILVER AND TITANIUM DIOXIDE BASED OPTICALLY TRANSPARENT ANTIMICROBIAL COATINGS AND RELATED METHODS

CROSS REFERENCE TO RELATED APPLICATIONS

This application is a National Stage of International Application No. PCT/US19/37624, filed Jun. 18, 2019, which claims the benefit of U.S. Patent Application No. 62/686,865, filed Jun. 19, 2018, the contents of which are herein incorporated by reference.

BACKGROUND

Healthcare associated infections (HAIs), also known as nosocomial infections, are one of the leading causes of patient morbidity and mortality in the United States. HAIs occur in all kinds of healthcare settings via direct and indirect causes, including transmission of pathogens among the patients and healthcare workers, postoperative complications, and contact with contaminated surfaces.

HAIs can be reduced by following proper disinfection strategies. Although partially effective, conventional disinfection strategies, such as using chemical cleaning products and disinfectants, do not provide full protection against all hospital acquired diseases. Occurrences of antibiotic-resistant bacteria, including *Pseudomonas aeruginosa* (*P. aeruginosa*), *Clostridium difficile* (*C. difficile*), and methicillin resistant *Staphylococcus aureus* (MRSA), in healthcare facilities across the United States are on the rise, reducing the reliability of conventional bacterial disinfection methods.

BRIEF DESCRIPTION OF THE DRAWINGS

Illustrative embodiments of the disclosure will hereafter be described with reference to the accompanying drawings.

FIG. 1A shows a TEM image of SWCNTs/A25. FIG. 1B shows a TEM image of SWCNTs/A100. FIG. 1C shows a TEM image of n-Ag/A25. FIG. 1D shows a TEM image of n-Ag/A100.

SUMMARY

Provided are methods of reducing microbial attachment to a surface using antimicrobial coatings, methods of making the antimicrobial coatings and the antimicrobial coatings themselves.

Methods of reducing microbial attachment to a surface are provided. In embodiments, such a method comprises illuminating a surface comprising a substrate and a coating on the substrate with ultraviolet light, wherein the coating comprises anatase titanium dioxide nanoparticles functionalized with silver nanoparticles and is optically transparent to visible light; and exposing the illuminated surface to microbes. The coating exhibits a reduction in microbial attachment as compared to the coating absent the illumination.

Methods of making antimicrobial surfaces are also provided. In embodiments, such a method comprises applying a suspension of anatase titanium dioxide nanoparticles functionalized with silver nanoparticles to a substrate to form a coating thereon, wherein the coating is optically transparent to visible light and wherein the coating exhibits a reduction in microbial attachment under illumination with ultraviolet light as compared to the coating absent the illumination.

Antimicrobial surfaces are also provided. In embodiments, such a surface comprises a substrate and a coating thereon, the coating comprising anatase titanium dioxide nanoparticles functionalized with silver nanoparticles, wherein the coating is optically transparent to visible light and wherein the coating exhibits a reduction in microbial attachment under illumination with ultraviolet light as compared to the coating absent the illumination.

DETAILED DESCRIPTION

Coatings composed of anatase titanium dioxide ($TiO_2$) nanoparticles having even smaller silver nanoparticles (n-Ag) bound thereto are provided. Also provided are antimicrobial surfaces made by applying the coatings to a substrate surface. The coatings are optically transparent and are characterized by low bacterial attachment as well as high bacterial kill percentages (% kill). The surprisingly low bacterial attachment is particularly useful since, if bacteria do not attach to a surface, they do not need to be destroyed. The coatings have applications as self-cleaning coatings on display screens for electronic devices, medical equipment, or any other substrates for which antimicrobial properties are important.

Figure 6:
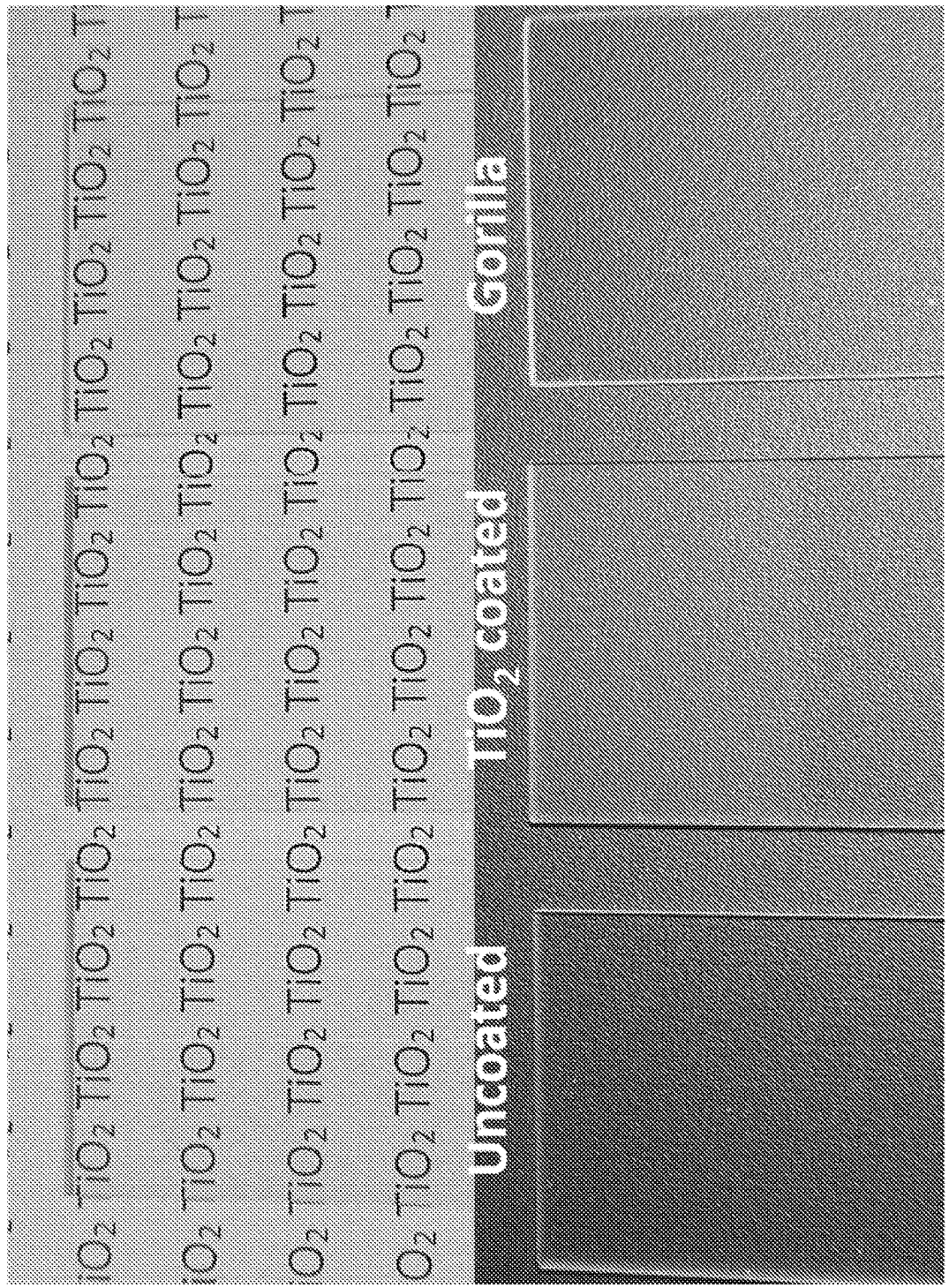
FIG. 6 shows a transparency comparison of uncoated sample, $TiO_2$ coated sample, and regular Gorilla® glass sample on a "$TiO_2$" printed and black background.
Figure 7:
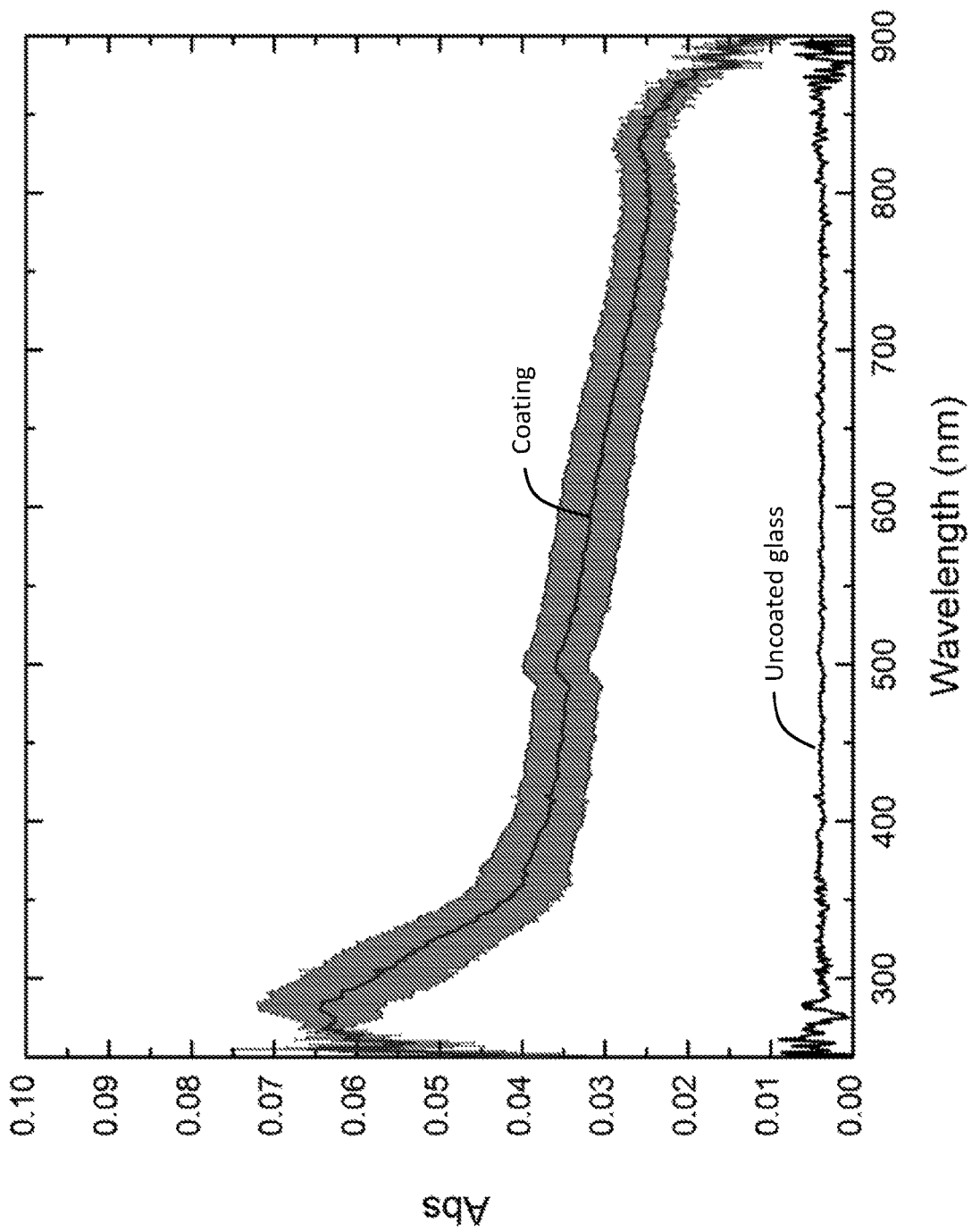
FIG. 7 is a plot of absorbance versus wavelength for an AA100 sample having greater than 50% area coverage, confirming that the coating is optically transparent to visible light.

By "optically transparent," it is meant optically transparent to visible light, i.e., light having a wavelength in a range of from 400 nm to 700 nm. Optical transparency can be confirmed using an spectrometer, measuring the coating's absorbance over a wavelength range of from 400 nm to 700 nm, and calculating an average transmission of the light over this wavelength range. Optically transparent coatings are characterized by an average transmission of light over this wavelength range that is greater than 99%, greater than 99.5%, or greater than 99.9%. When the optically transparent coatings are used on substrates such as display screens, this means that the information on the display screen is readily visible to the user. Optically transparent coatings comprising anatase $TiO_2$ nanoparticles are shown in FIG. 6 and the optical transparency is confirmed from absorbance measurements as shown in FIG. 7. It is noted that many conventional $TiO_2$-based coatings are not optically transparent, but are rather opaque or white.

When $TiO_2$ particles are activated by photoexcitation, electrons from the valence band migrate to the conduction band, creating electron deficiencies, also referred to as holes, in the valence band. The charges either recombine or transfer to the $TiO_2$ surface to undergo reduction and oxidation (redox) reactions with surface species, and thereby generate reactive oxygen species (ROS), including hydroxyl radicals, hydrogen peroxide, and superoxide ions.

The $TiO_2$ nanoparticles kill target bacteria and other microbes via peroxidation and disruption of phospholipids and lipopolysaccharides within bacterial cell membranes. Bacterial cell lysis leads to the leakage and exposure of cell organelles and genetic materials to the ROS. Due to the non-specificity of the ROS in disrupting the structural proteins found in the outer surface of the target bacteria, bacterial resistance to photocatalytic treatment is unlikely to occur. In addition to its bactericidal property, photocatalytically active $TiO_2$ also exhibits photoinduced super-hydrophilicity (PSH). This may contribute, at least in part, to resisting bacterial attachment and reducing biofilm formation at its surface.

$TiO_2$ nanoparticles are characterized as having diameters (particle sizes) of no greater than 1000 nm. However, the anatase $TiO_2$ nanoparticles in the coatings typically have diameters substantially smaller than 1000 nm. For example, in some embodiments of the coatings, the average diameter of the anatase $TiO_2$ particles is less than 200 nm. By way of illustration, the average diameter of the anatase $TiO_2$ particles in some of the coatings is in the range from 20 nm to 50 nm or from 50 nm to 150 nm. This includes embodiments of the coatings in which the average diameter for the anatase $TiO_2$ particles is in the range from 60 nm to 120 nm and further includes embodiments of the coatings in which the average diameter for the anatase $TiO_2$ particles is in the range from 80 nm to 110 nm or from 90 nm to 100 nm. By average diameter it is meant an average over a representative number of $TiO_2$ particles. The average diameter may be determined from XRD spectra and TEM images as described in the Example, below.

As noted above, the $TiO_2$ of the $TiO_2$ nanoparticles is in the anatase form and the presence of other phases, e.g., the rutile phase, may be zero, immeasurable, or too small to have a material effect on the properties of the $TiO_2$. Confirmation that the $TiO_2$ nanoparticles are pure anatase may be obtained using XRD spectra as described in the Example, below.

In the coatings, the performance of the $TiO_2$ nanoparticles is further enhanced by attaching silver nanoparticles to the $TiO_2$ nanoparticles. The resulting Ag surface-functionalized $TiO_2$ nanoparticles (n-Ag/$TiO_2$) can provide the coatings with increased antimicrobial photocatalytic activity because the n-Ag can serve as electron sinks to retard charge recombination, and n-Ag surface plasmons can be excited by light in the visible range and produce reactive oxygen species at its surface or induce energy transfer to the $TiO_2$ to create electron and hole pairs for additional surface reactions. Moreover, n-Ag has its own antimicrobial properties. The silver nanoparticles are smaller than the $TiO_2$ particles to which they are bound, typically having average diameters of no greater than 50 nm, including diameters no greater than 30 nm. For example, in some embodiments of the coatings, the average diameter of the silver particles is in the range from 3 nm to 30 nm. The average diameter may be determined from TEM images as described in the Example, below.

The relative amounts of silver and titanium dioxide in the coatings can vary. By way of illustration, some embodiments of the coatings have a mass ratio of Ag to $TiO_2$ in the range from about 1:10 to 1:150 (i.e., mass Ag:mass $TiO_2$). This includes embodiments of the coatings having a mass ratio of Ag to $TiO_2$ in the range from about 1:60 to 1:140 and further includes embodiments of the coatings having a mass ratio of Ag to $TiO_2$ in the range from about 1:60 to 1:100, 1:10 to 1:80, and 1:10 to 1:60. The mass ratio values can refer to the values used based on the amounts during synthesis.

The $TiO_2$ nanoparticles can be functionalized (decorated) with Ag nanoparticles by exposing a mixture of anatase $TiO_2$ nanoparticles and a silver salt in an organic solvent (e.g., ethanol, acetone, etc.) to UV light. The conditions of exposure (e.g., wavelength, intensity, time) are selected to induce reduction of silver ions and silver nanoparticle formation on the surface of the anatase $TiO_2$ nanoparticles. Illustrative conditions are described in the Example, below. It has been found that the following conditions are useful for optimizing functionalization: minimizing/eliminating $O_2$ during functionalization; use of ethanol as the organic solvent; and limiting the amount of n-Ag relative to $TiO_2$ (e.g., a mass ratio of 1:10 is useful).

The coatings can be formed on a substrate by applying a suspension of the silver-functionalized $TiO_2$ nanoparticles to a surface of a substrate and allowing it to dry. Although the suspension can be applied using a variety of thin film coating techniques, dip coating is advantageous for ensuring a homogeneous distribution of the n-Ag/$TiO_2$ nanoparticles while minimizing aggregation/root-mean-square (RMS) roughness even at the high percent area coverages described below.

The substrates on which the coatings can be formed may be composed of a variety of materials including glass (for example, borosilicate glass), ceramics, metals (for example, stainless steel or titanium), and painted substrates.

Figures 5A, 5B:
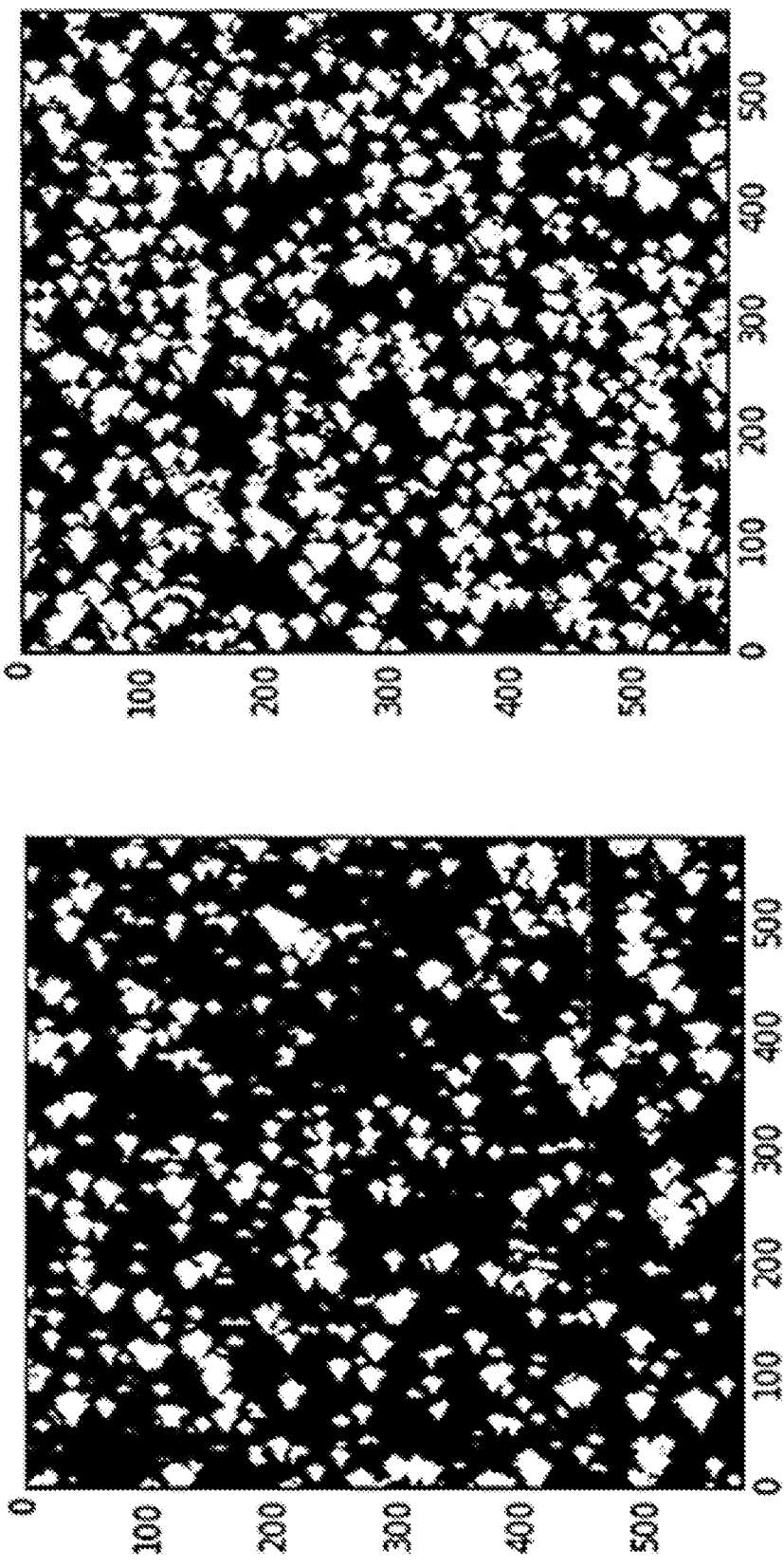
FIGS. 5A-5D depict surface coverage analysis based on the AFM images of the A100 coated samples prepared via dip-coating 2 times in 1 g/L A100 solution (FIG. 5A); 4 times in 500 mg/L A100 solution (FIG. 5B); 8 times in 250 mg/L A100 solution (FIG. 5C); and 10 times in 250 mg/L A100 solution (FIG. 5D). A100 particles in the images shown in FIGS. 5A and 5B are relatively larger and more sparsely dispersed than those in the images shown in FIGS. 5C and 5D.
Figure 5C:
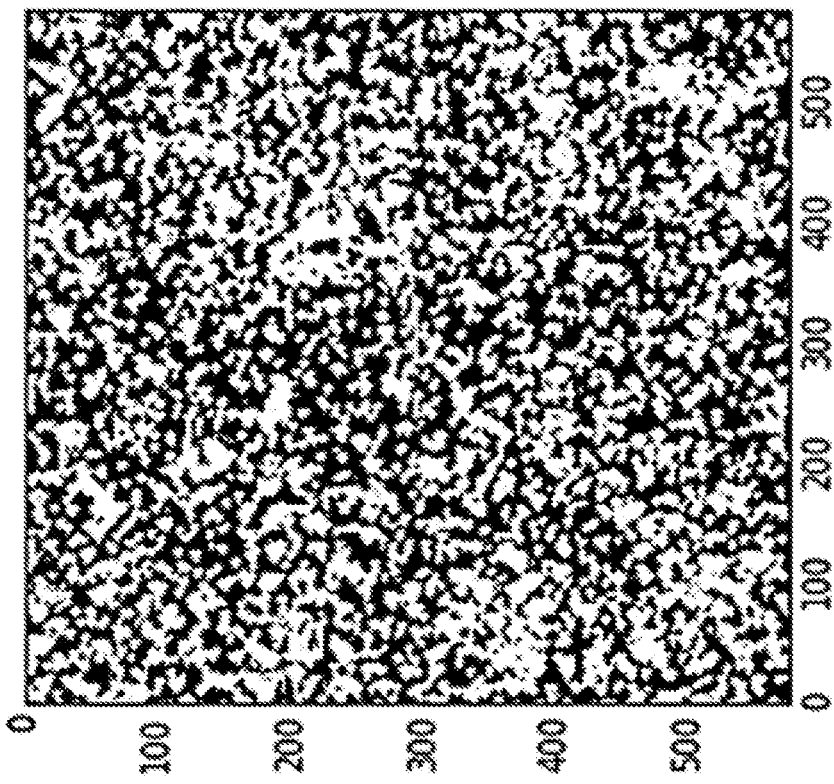
Figure 5D:
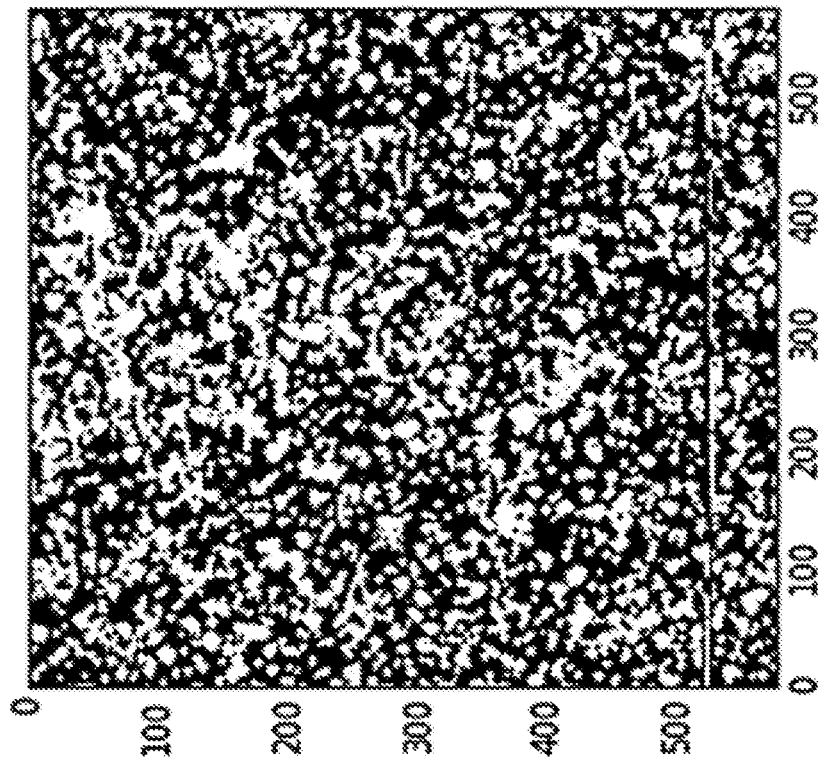

The coatings may be characterized by their percent area coverage of the silver-functionalized $TiO_2$ nanoparticles over the surface of a substrate. Percent area coverage may be determined from AFM images as described in the Example below. The percent area coverage may be at least 40%, at least 50%, at least 60%, or in a range of from 40% to 60%. FIG. 5D shows an AFM image of a substrate having a percent area coverage of the silver-functionalized $TiO_2$ nanoparticles of 50%. The homogeneous distribution and lack of aggregation in the coating is evident from the image. At the same time, this illustrative coating is optically transparent.

The lack of aggregation of silver-functionalized $TiO_2$ nanoparticles may also be confirmed by measuring the RMS roughness of the coatings as described in the Example below. The coatings may be characterized has having an RMS roughness that is no greater than the average size of the $TiO_2$ nanoparticles of the coatings. In embodiments, the coating has an RMS roughness in a range of from 80 nm to 110 nm or 80 nm to 100 nm.

The coatings may consist essentially of, or consist of, the silver-functionalized $TiO_2$ nanoparticles. The coatings generally do not include other materials, e.g., oligomers, polymers, $SiO_2$ (or silica precursors such as tetraethoxysilane), or other capping agents conventionally used in functionalizing $TiO_2$ nanoparticles such as tert-butylcalix[4]arene.

As demonstrated in the Example, below, the coatings exhibit antimicrobial properties even under dark conditions, but their antimicrobial properties can be enhanced by exposure to UV light. By dark conditions it is meant in the absence of all light, including UV light. As noted above, at least some embodiments of the coatings demonstrate surprisingly low bacterial attachment upon exposure to UV light. (See, e.g., AA100 of FIG. 4A.) Thus, in one aspect, the present disclosure provides a method of reducing microbial attachment to a surface which comprises illuminating a surface comprising a substrate and one of the disclosed coatings on the substrate with UV light and exposing the illuminated surface to microbes, wherein the coating exhibits a reduction in microbial attachment as compared to the coating absent the illumination. The phrase "absent the illumination" may refer to "dark conditions" as described above.

The illumination step may use UV light having a wavelength in a range of from 100 nm to less than 400 nm. The UV light can come from a UV-emitting light source, such as the sun (i.e., solar light), a light-emitting diode (LED), or a xenon arc lamp. The period of illumination may vary but may be in a range of from a few seconds to minutes to hours. For purposes of quantifying the efficacy of the coating, however, an illumination step may use UV light from a 1,000 W xenon arc lamp for 45 minutes. Other conditions, e.g., distance of the coating from the UV light, may be as described in the Example, below.

The microbes in the exposure step may be of any variety and may result from, e.g., touching, splattering, spilling, spraying, etc., the illuminated surface with a fluid or other sample containing the microbes. The microbes may be bacteria of any variety. However, for purposes of quantifying the efficacy of the coating, the microbes of an exposure step may be *Escherichia coli* (*E. coli*) ATCC 25922 bacteria which may be provided as a fluid sample as described in the Example, below. The illumination and exposure step may overlap partially or completely in time or the illumination step may be fully completed prior to the exposure step.

As noted above, illumination of the coating reduces the number of microbes that attach to the coating as compared to the number of microbes that attach to the coating in the absence of the illumination. This comparison is done using the same coating and the same conditions except employs dark conditions (no light, including no UV light). Microbial attachment may be measured and the reduction calculated as described in the Example, below.

Figure 4A:
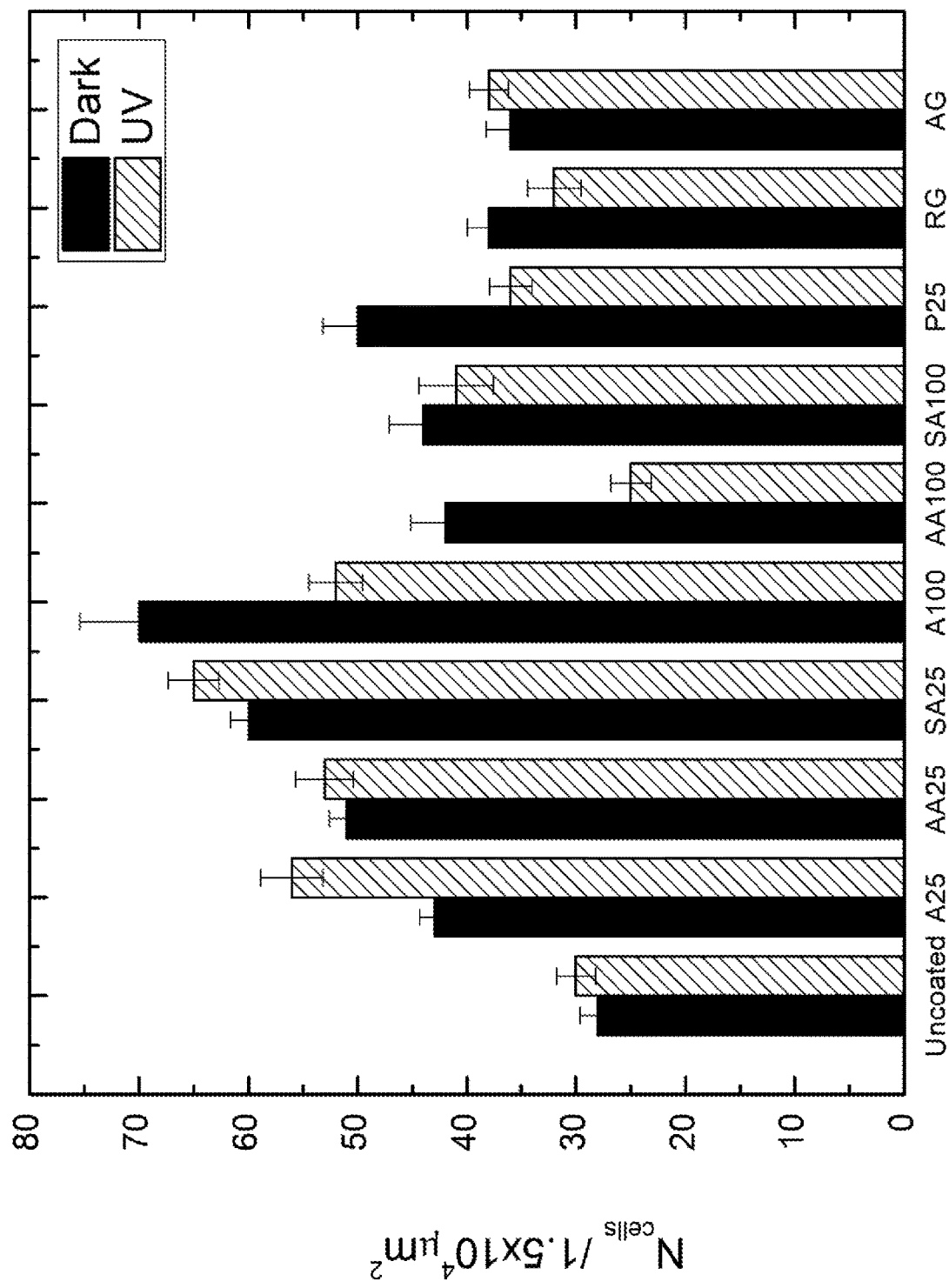
FIG. 4A depicts antimicrobial screening for bacterial attachment.

Some embodiments of the coatings reduce microbial attachment by at least 30%, at least 35%, or at least 40% as compared to the coatings absent the illumination with UV light. (See, e.g., AA100 in FIG. 4A showing a reduction in microbial attachment of about 40% under UV illumination as compared to AA100 under dark conditions.) In embodiments, the coatings exhibit an *E. coli* ATCC 25922 attachment of no greater than 30 cells/$1.5 \times 10^4$ $\mu m^2$ or no greater than 27 cells/$1.5 \times 10^4$ $\mu m^2$ under illumination with UV light from a 1,000 W xenon arc lamp for 45 minutes. Other illumination conditions and details of the microbial attachment and measurement may be those described in the Example, below. By comparison, the same coatings may exhibit greater *E. coli* ATCC 25922 attachment, but no greater than 50 cells/$1.5 \times 10^4$ $\mu m^2$ or no greater than 46 cells/$1.5 \times 10^4$ $\mu m^2$ under dark conditions.

The coatings may also be characterized based on the % kill for *E. coli* ATCC 25922 under dark conditions and under UV illumination conditions. Again, determination of % kill may follow the details provided in the Example, below. Some embodiments of the coatings have a % kill for *E. coli* ATCC 25922 of at least 10% under dark conditions and a % kill for *E. coli* ATCC 25922 of at least 80% under UV illumination. This includes embodiments of the coatings having a % kill for *E. coli* ATCC 25922 of at least 15% under dark conditions and a % kill for *E. coli* ATCC 25922 of at least 85% under UV illumination.

Another advantageous feature of the coatings is that they may be regenerated by UV illumination so that they can provide continued antimicrobial properties, including reduced microbial attachment, upon additional exposure to microbes. For example, upon exposure to a fluid, e.g., water, silver ions from the silver nanoparticles attached to the $TiO_2$ nanoparticles can leach into the fluid. Instead of otherwise being lost, these silver ions may be recaptured and reattached to the $TiO_2$ nanoparticles by photoreduction of the silver ions to elemental silver via the UV illumination. The regenerated coating may also exhibit a reduction in microbial attachment after exposure to microbes which may be the same as the initial reduction (prior to regeneration). This means the coatings may be used multiple times and can have long life-times as compared to conventional antimicrobial coatings. This is particularly advantageous for using the coatings as permanent films on display screens.

Unless otherwise indicated, measured and measurable properties disclosed herein refer to those properties measured at room temperature (23° C.) and atmospheric pressure.

EXAMPLE

In this Example, optically transparent n-Ag/$TiO_2$ coatings were developed that can be used to provide surface disinfection for touchscreens and make medical devices self-cleaning as additional buffers to control transmission of diseases in clinical settings. The overall performance of the optically transparent n-Ag/$TiO_2$ coatings was also compared to that of other $TiO_2$-based coatings.

This Example demonstrates that optically transparent $TiO_2$ films can be made which impart antibacterial properties to glass and improve on the performance of the commercially available products. A variety of $TiO_2$-based transparent films were synthesized and characterized. The antibacterial action of commercially available pure and mixed phased-$TiO_2$ was compared with $TiO_2$ composites made with SWCNTs and n-Ag under both dark and UV illuminated conditions. Dip coating of borosilicate glass was employed to prepare optically transparent $TiO_2$ films whose surface properties were evaluated with atomic force microscopy (AFM) and contact angle analysis. Finally, bacterial attachment and bactericidal performance of the $TiO_2$ coated samples were compared with the regular and antimicrobial Corning® Gorilla® Glass.

Material Preparation

Three samples of commercial $TiO_2$, including anatase-$TiO_2$ of two different particle sizes (<25 nm, 99.7%; <100 nm, 99.8%; Sigma-Aldrich) and P25 (Aeroxide® P25; Acros Organics), were used without further purification. P25 was not used for synthesis because it is already a composite of anatase-$TiO_2$ (70%) and rutile-$TiO_2$ (30%). Nanocomposites of $TiO_2$ and SWCNTs were synthesized from the commercial anatase-TiO$_2$ and acid treated using functionalized SWCNTs via the hydration-dehydration method. 10 mg of SWCNTs and 200 mg of anatase-TiO$_2$ (SWCNTs to TiO$_2$, mass ratio of 1:20) were sonicated in 150 mL of Milli-Q water for 10 minutes. The SWCNTs and TiO$_2$ suspension was then heated to 80° C. on a heated stir plate until the water was evaporated. The SWCNTs/TiO$_2$ composite was dried in an oven at 104° C. overnight to ensure complete evaporation of the water.

The n-Ag/TiO$_2$ composite was prepared via a photo-deposition method but without modifying the TiO$_2$ surface with capping agents (e.g., calixarene and tetraethyl orthosilicate). Briefly, 100 mg of AgNO$_3$ (≥99.0%; Sigma-Aldrich) and 1 g of anatase-TiO$_2$ (AgNO$_3$ to TiO$_2$ mass ratio of 1:10) were sonicated in 100 mL of ethanol in a round bottom flask for 10 minutes to break any large agglomerates. The AgNO$_2$ and TiO$_2$ suspension was then stirred at 500 rpm for 20 minutes with N$_2$ purging to remove dissolved oxygen. Aluminum foil was wrapped around the flask to avoid direct light exposure throughout the synthesis. The photodeposition of Ag nanoparticles was carried out by submerging the UV lamp (365 nm; 1.2 W/cm$^2$; UV Pen-ray) into the flask, illuminating the flask for 30 minutes during N$_2$ purging, and stirring. After the photodeposition, the n-Ag/TiO$_2$ composite was filtered using vacuum filtration and washed with 200 mL of ethanol. The filtered n-Ag/TiO$_2$ was then dried in oven at 104° C. overnight.

Material Characterization

X-ray diffraction (XRD) analysis of anatase-TiO$_2$ was carried out on a Rigaku Dmax powder diffractometer equipped with a copper k-alpha source to confirm its phase and average crystallite size. The sample was scanned from diffraction angles of 20° to 60° (θ) with a step size of 0.1°. MDI Jade9 software was used to analyze the XRD patterns and identify the phase and composition of the TiO$_2$ nanoparticles. The TiO$_2$ nanoparticle size was calculated using the Scherrer equation. The Brunauer-Emmett-Teller (BET) method was carried out on a Micrometrics ASAP 2020 to measure the surface area of anatase-TiO$_2$ via N$_2$ physisorption. To determine the presence and concentration of trace metals and other contaminants in anatase-TiO$_2$, inductively coupled plasma mass spectrometry (ICP-MS) analysis was carried out on a Thermo iCAP Q ICP-MS. Anatase-TiO$_2$ was dissolved in HF/HNO$_3$ solution and ICP-MS grade HCl solution was used as a blank. The total mass of the constituents of anatase-TiO$_2$ and their weight percents were calculated.

The electron microscopy images of the SWCNTs/TiO$_2$ and n-Ag/TiO$_2$ were taken using a Hitachi H-8100 transmission electron microscope (TEM) operated at 200 kv. TEM samples were prepared by allowing a drop of TiO$_2$ composite dispersed in ethanol to air-dry on a Formvar removed TEM copper grid. The energy-dispersive X-ray (EDX) analysis was performed on a Hitachi SU8030 scanning electron microscope (SEM) at 2.0 kV to determine the chemical compositions of n-Ag/TiO$_2$ in spectral imaging (element mapping) mode.

Material Photoactivity Screening

Photoactivity screening of the TiO$_2$ composites was evaluated by measuring the degradation rate of methylene blue (powder; Merck & Co., Inc.) dissolved in Milli-Q water. 10 mg of TiO$_2$ composite was suspended in 100 mL of Milli-Q water, and then 600 μL of 500 mg/L methylene blue solution was added to the TiO$_2$ suspension. The TiO$_2$ suspension with methylene blue was stirred at 500 rpm for 30 minutes in the dark to allow adsorption of methylene blue on TiO$_2$ nanoparticles. After the dark adsorption of methylene blue, the suspension was exposed to the UV light (Blak-Ray™ 100 W longwave mercury spot lamp; UVP, LLC) while being stirred at 500 rpm. Samples were taken before 30 minutes of the dark adsorption and every 5 minutes up to 60 minutes of the UV irradiation. Collected samples were centrifuged at 11,500 rpm for 10 minutes to separate the TiO$_2$ nanoparticles from the methylene blue solution. The sample absorbance data, at 660 nm with a Milli-Q water blank, were collected and fitted to kinetic curves to find the reaction rates.

Coating Procedure and Characterization

Optically transparent TiO$_2$ coatings were made on a borosilicate glass substrate via a dip-coating technique. Prior to the deposition of the TiO$_2$, the glass substrate was submerged and sonicated in the 1 wt % Alconox solution, Milli-Q water, acetone, and methanol bath for 10 minutes each to remove dirt and grease. The cleaned glass substrate was etched in 6.0M HCl solution for 30 minutes and rinsed with Milli-Q water. The dip-coating solution was prepared by suspending the TiO$_2$ composites in ethanol for 20 minutes in a sonicator. 250 mg/L dip-coating solutions were prepared and the glass substrates were dipped 10 times with a withdrawing speed of 1 mm/s. The TiO$_2$ suspension was sonicated for 5 minutes after every dipping to keep the TiO$_2$ nanoparticles well suspended. Since ethanol is relatively volatile compared to water, the samples were air dried after each dipping and calcined in a furnace for 2 hours at 200° C. for the SWCNTs/TiO$_2$ coated samples and 400° C. for the other TiO$_2$ coated samples.

The surface topography and roughness of the TiO$_2$ coated samples were analyzed using Bruker Dimension FastScan atomic force microscopy (AFM) equipped with a Bruker Broadband™ air and fluid cantilever. All AFM images were taken at a scan rate of 20 Hz in the air-tapping mode. NanoScope Analysis software was used to obtain surface topography images and the roughness of the TiO$_2$ coated samples. A Python based image analysis tool was used to determine the percentage of the area coverage of the TiO$_2$ on the samples, based on AFM images. The hydrophilicity of the TiO$_2$ coatings was measured with sessile water drop shape analysis using a Kruss model DSA100 drop shape analysis system. Deionized water was dropped onto the TiO$_2$ coated surface at a rate of 3 μL/min. The contact angle of the water droplet on the TiO$_2$ surface was measured with a circle fitting method before and after 45 minutes of the UV irradiation to evaluate the effect of the photoinduced superhydrophilicity of the TiO$_2$ coatings.

Cell Attachment and Viability Screening

Cell attachment and viability screening tests were done in water as preliminary tests to assess the antimicrobial efficacy of the uncoated and TiO$_2$ coated samples. A well-characterized strain of *E. coli* ATCC 25922 was selected as test bacteria and cultured as follows. *E. coli* ATCC 25922 was grown on an LB plate overnight at 37° C. until visible colonies of *E. coli* formed on the plate. A single colony of *E. coli* was inoculated into 75 mL of a fresh LB media and incubated overnight. 1 mL of the overnight culture was inoculated into another 75 mL of fresh LB media and incubated for around 2.5 hours at 37° C. and 100 rpm until the bacteria reached mid-exponential phase (OD$_{600}$=0.4–0.5). 1 mL of the 2.5 hr bacterial culture was centrifuged at 8000 rpm for 3 min to separate the bacteria and supernatant. The bacteria were re-suspended and centrifuged in 1 mL of 0.85% NaCl physiological solution twice to wash away the remaining LB media. The bacterial suspension was re-suspended and diluted in 0.85% NaCl solution until $OD_{670}$ reached between 0.70 and 0.80 (cell concentration of approximately $10^8$ CFU/mL).

For the cell attachment and viability screening, the $TiO_2$ coated glass sample was placed in a small petri-dish filled with 3 mL of the $10^8$ CFU/mL bacterial suspension. The small petri-dish was covered with a UV transparent film (Axygen Platemax® UltraClear Sealing Film) to minimize evaporation during UV exposure. A multi-sun solar simulator (Newport Model 66921) equipped with a 1,000 W xenon lamp that provides high intensity UV to near-infrared light output was used as the light source. The $TiO_2$ coated sample submerged in the bacterial suspension was placed 20 cm below the light source and exposed to the UV light for 45 minutes while being rigorously shaken at 300 rpm. After the UV exposure, 9 μL of the BacLight reagent (LIVE/DEAD™ BacLight™ L7007; ThermoFisher) was added to the bacterial suspension to stain the bacterial cells. Syto-9 nucleic acid and propidium iodide in the BacLight reagent stain live and dead cells in green and red, respectively. The $TiO_2$ coated sample was gently washed with Milli-Q water to remove unattached bacterial cells because the preliminary test focused on the interaction between the surface and the attached bacteria. Bacterial attachment and viability screening were conducted on the $TiO_2$ coated samples using a Leica DM5500 B microscope equipped with a QImaging Exi Aqua™ camera and Leica HC PL APO 63×/1.40 objective lens. Obtained fluorescent images of the bacteria were analyzed with MetaMorph® imaging software. Based on the fluorescent images, a paired sample t-test was conducted to determine if the bacterial attachment and viability screening results of the samples had statistically significant difference at p value of 0.05.

Material Characterization

Prior to using the two commercial anatase-$TiO_2$ samples for synthesis of composites, they were characterized using XRD, BET, and ICP-MS. Table 1 summarizes the characterization data of the base $TiO_2$ materials: anatase-$TiO_2$<25 nm, denoted as A25; and anatase-$TiO_2$<100 nm, denoted as A100. Both A25 and A100 have 2θ peaks at 25°, 38°, 48°, and 54°, indicating that they are pure phase anatase-$TiO_2$ (data not shown). Using the Scherrer equation, the crystallite sizes of the A25 and A100 were calculated to be around 13.5±1.1 nm and 87.6±10.4 nm, respectively. Based on the BET analysis, the surface area of the A25 was 166.7±0.8 $m^2/g$, and the surface area of the A100 was 15.4±0.1 $m^2/g$. These results were expected, since smaller particles typically have larger surface areas compared to larger particles, providing more reaction sites for photocatalytic activity. The ICP-MS analysis of the A25 and A100 revealed that they contained small amounts of metal impurities such as zirconium, niobium, and antimony (data not shown). Although both formulations showed greater than 99% purity based on the ICP-MS result, A25 had higher levels of metal impurities than A100. Metal impurities in $TiO_2$ may increase photocatalytic performance by retarding electron-hole pair recombination and/or enhancing the light absorption in the visible range. Conversely, depending on the specific impurity type and concentration, they may also decrease the photocatalytic performance of $TiO_2$ by creating recombination centers and increasing electron-hole pair recombination rates.

TABLE 1

Material characterization data of the unmodified base $TiO_2$ materials

| Sample | Crystallite size (nm) | Surface area ($m^2/g$) | Purity (%) |
|---|---|---|---|
| A25 | 13.5 ± 1.1 | 166 ± 0.8 | >99 |
| A100 | 87.6 ± 10.4 | 15.4 ± 0.1 | >99 |
| Degussa P25* | 50 | 50 ± 15 | Anatase phase ~70% Rutile phase ~30% |

*Degussa P25 data are obtained from previously published data. (See, e.g., Tong, T., et al., Water research, 2013. 47(7): p. 2352-2362.)

TEM images of anatase-$TiO_2$ composites are shown in FIGS. 1A-1D. Based on the TEM images, the A25 nanoparticles were below 20 nm in size, except for a few large particles, while the A100 nanoparticles were predominantly 100 nm in size. In both cases, then, the TEM data are consistent with the XRD size characterization. In FIG. 1A, it is difficult to observe the SWCNTs in the A25 composite because smaller sized anatase particles were more difficult to disperse in solution and tended to aggregate into larger clusters, minimizing contact between the SWCNTs and individual A25 nanoparticles. On the other hand, the SWCNTs were clearly observable in FIG. 1B touching several A100 nanoparticles. Contact between the SWCNTs and the A100 would allow efficient electron trapping from the aggregated $TiO_2$ nanoparticles. In FIGS. 1C and 1D, silver nanoparticles with particle diameters between 3 nm and 20 nm were observed at the surface of the A25 and A100. Due to its small particle size, the A25 was decorated by one or two silver nanoparticles at most, whereas considerably more silver nanoparticles were well dispersed over the surface of the A100. The EDX analysis (spectral imaging) of the n-Ag/A25 and n-Ag/A100 confirmed that the silver nanoparticles were thoroughly dispersed and deposited on the surface of the anatase-$TiO_2$ (data not shown).

Material Photoactivity Screening

Figure 2A:
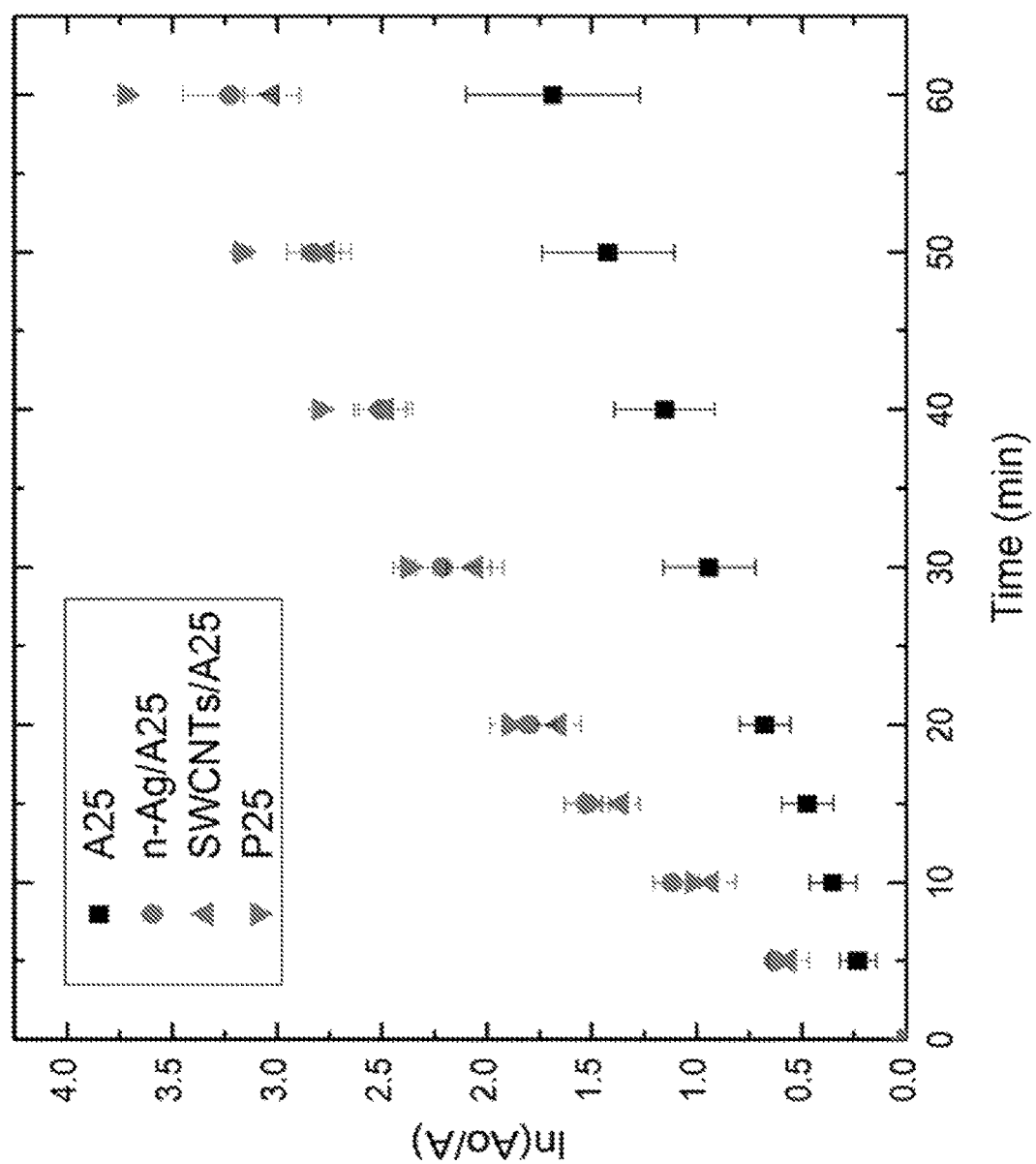
FIG. 2A depicts pseudo-first order linear transform of methylene blue degradation for A25 and modified A25 compared to P25.
Figure 2B:
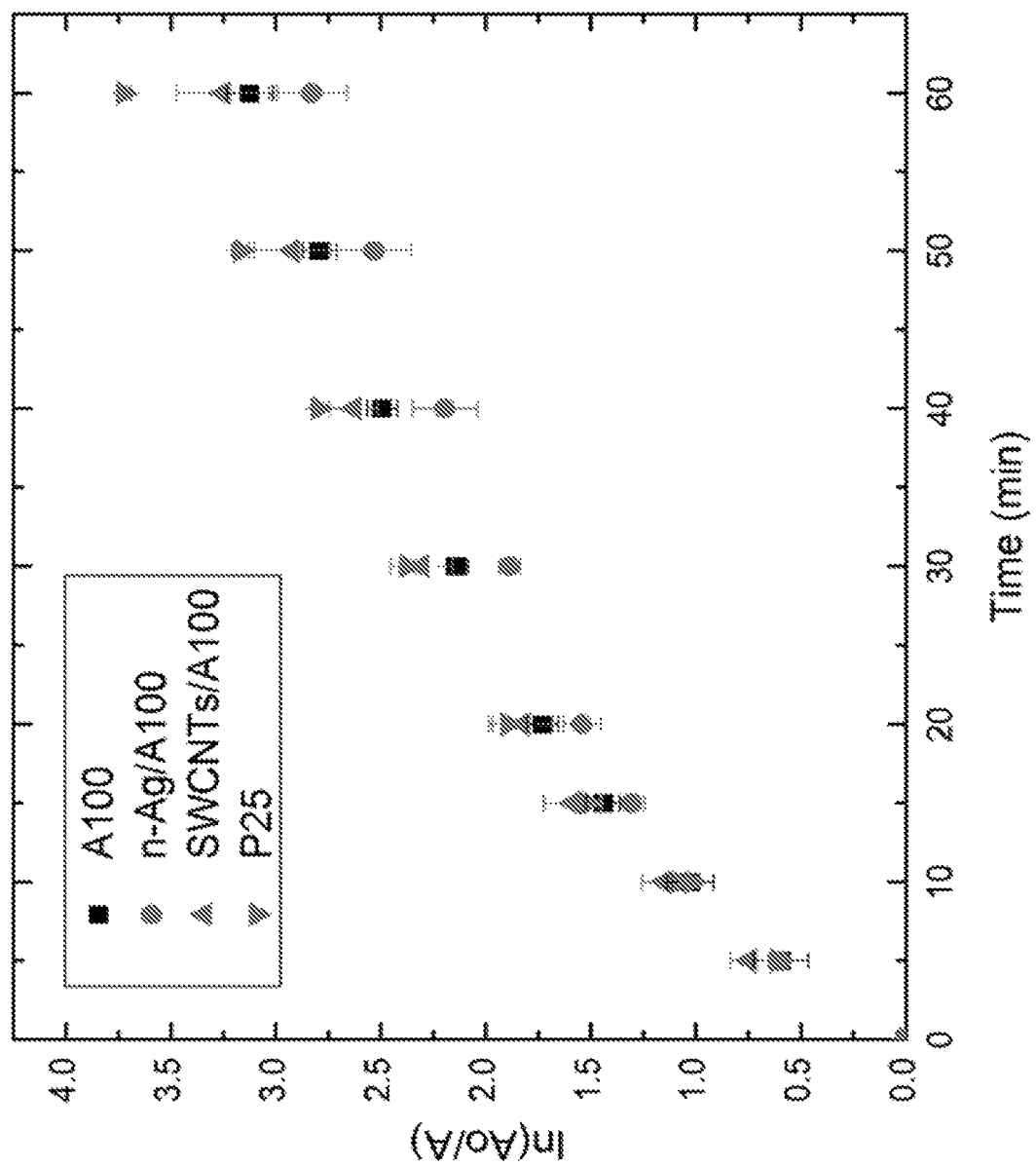
FIG. 2B depicts pseudo-first order linear transform of methylene blue degradation for A100 and modified A100 compared to P25.

Methylene blue decay curves for the modified and unmodified A25 and A100 are shown in FIGS. 2A and 2B, respectively, and compared to that of the P25. Rate constants are tabulated in Table 2 and indicate that modified A25 with the SWCNTs and n-Ag (SWCNTs/A25 and n-Ag/A25) improved methylene blue degradation rate constants in comparison to the unmodified A25. SWCNTs and n-Ag serve as electron sinks, hindering the electron-hole pair recombination rate and promoting photo-induced oxidation. n-Ag on the surface of $TiO_2$ also displays surface plasmon resonance due to visible light absorbance, extending the photo-response of the composite and enhancing ROS production.

TABLE 2

Comparison of pseudo first order rate constants for methylene blue decay by various $TiO_2$ materials

| | Kinetic constant, k ($10^{-2}$ $min^{-1}$) |
|---|---|
| A25 | 2.91 |
| n-Ag/A25 | 6.14 |
| SWCNT/A25 | 5.84 |
| A100 | 5.99 |
| n-Ag/A100 | 5.45 |
| SWCNT/A100 | 6.32 |
| P25 | 6.95 |

Coating Characterization

Figure 3A:
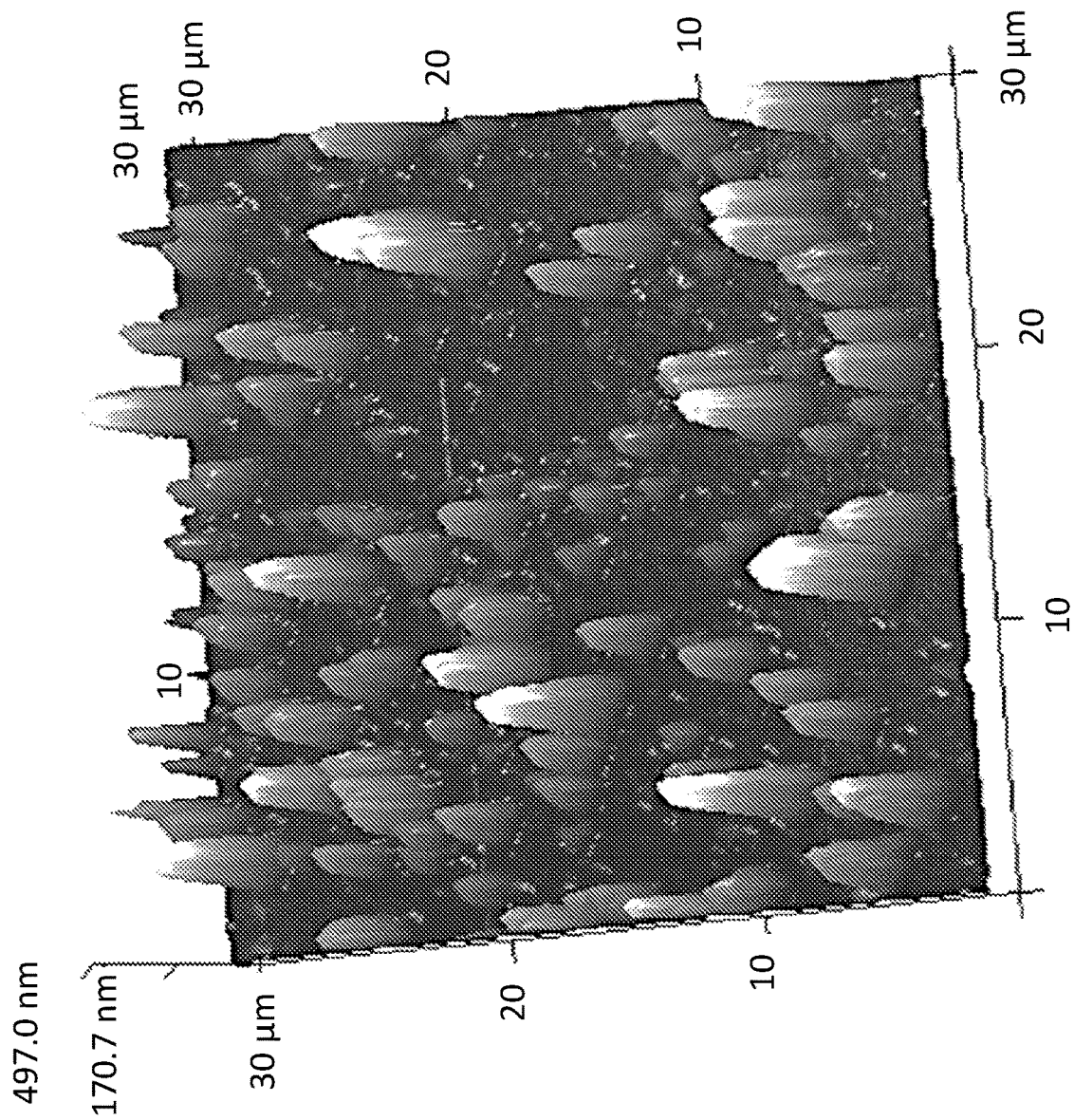
FIG. 3A shows an AFM image of A100 coated samples prepared via dipping 2 times in 1 g/L A100 solution.
Figure 3B:
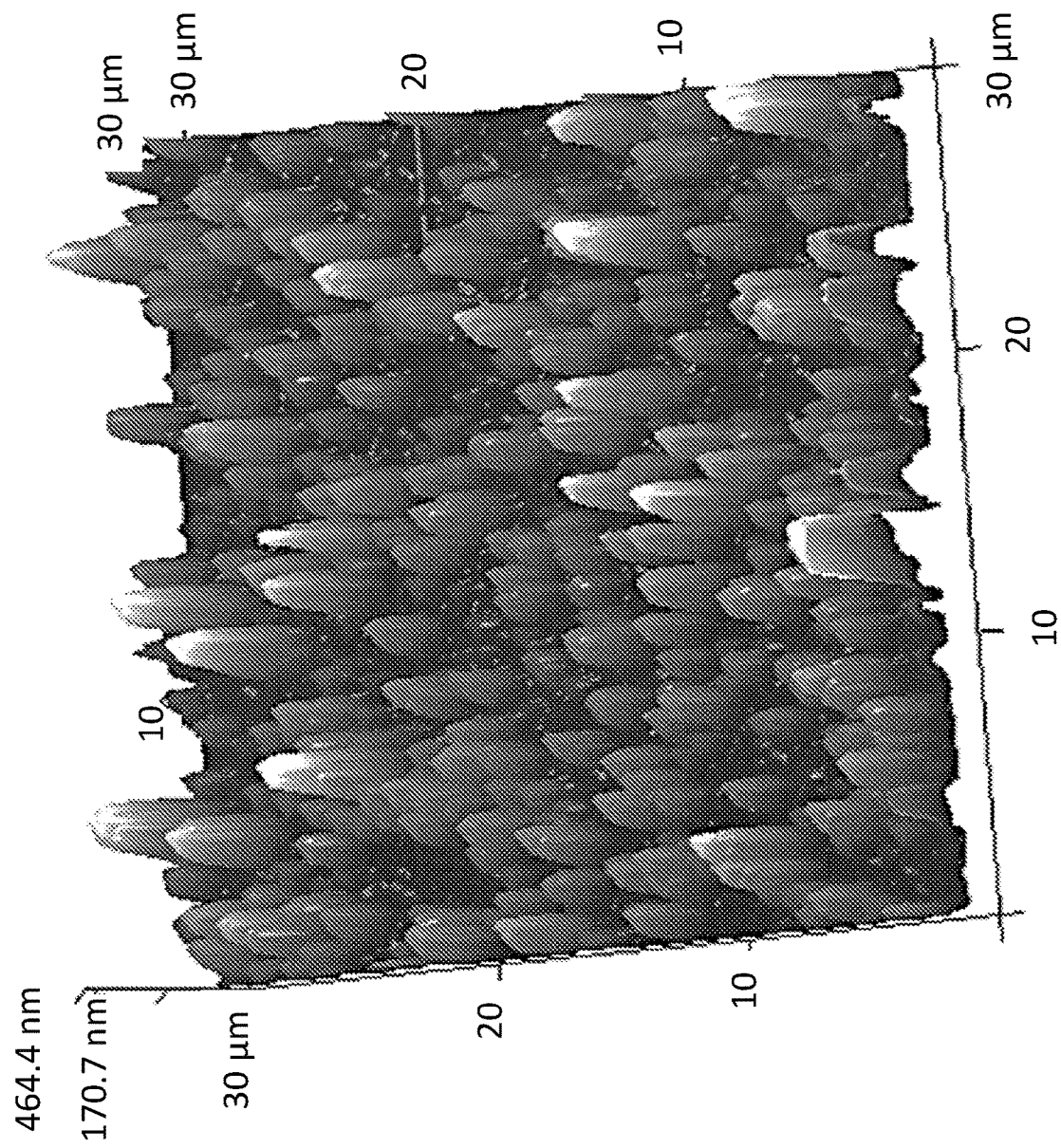
FIG. 3B shows an AFM image of A100 coated samples prepared via dipping 4 times in 500 mg/L A100 solution.
Figure 3C:
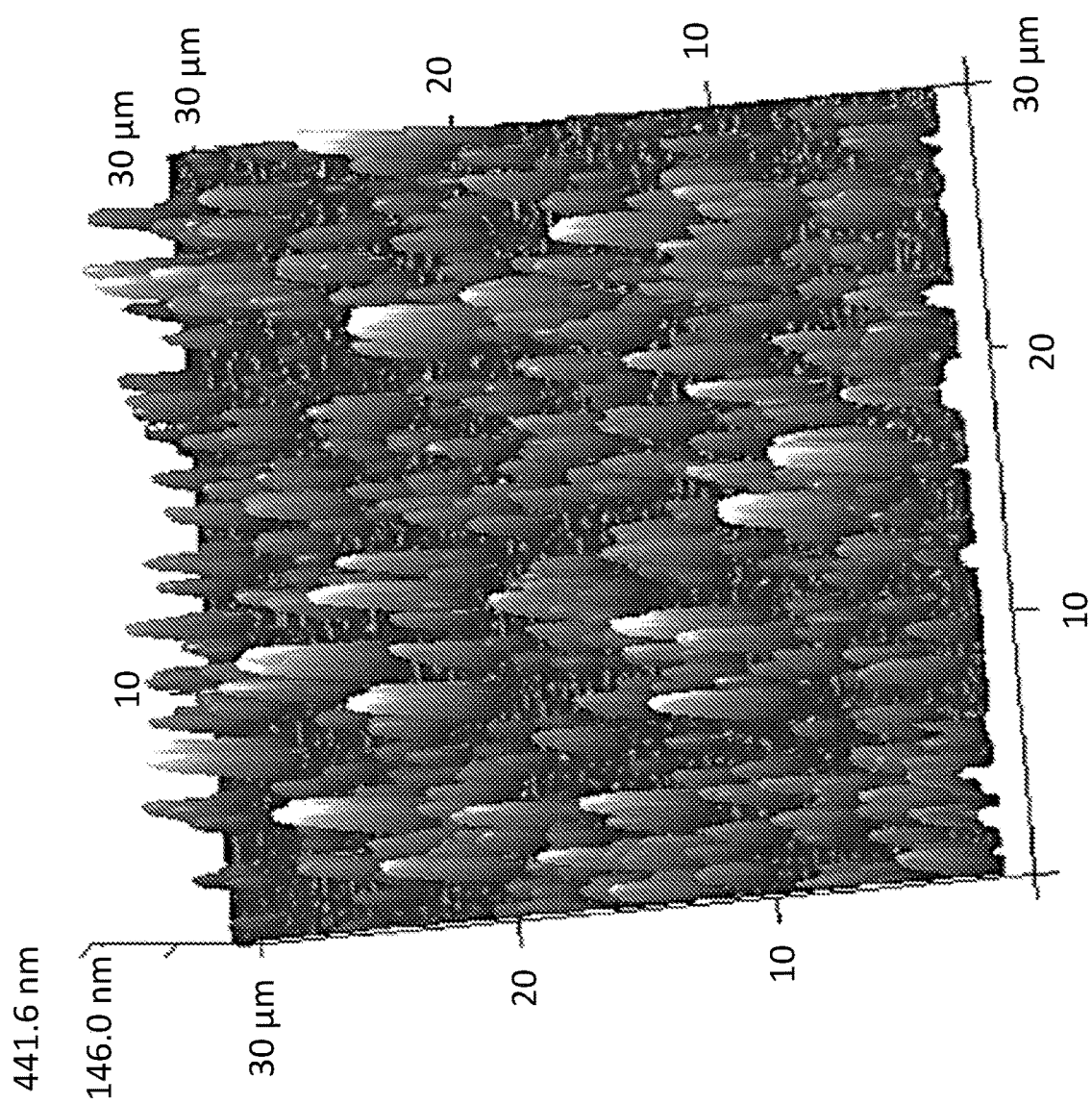
FIG. 3C shows an AFM image of A100 coated samples prepared via dipping 8 times in 250 mg/L A100 solution.

To maintain high optical transparency while maximizing TiO$_2$ coverage of the dip-coated samples, the coating treatment was optimized by varying the coating concentration and dipping repetition. AFM images of three A100-coated samples with different coating concentrations and dipping numbers are shown in FIGS. 3A-3C. The aggregate size of the deposited A100 increased as the solution concentration increased from 250 mg/L to 1 g/L. This was because A100 nanoparticles formed larger aggregates in a highly-concentrated solution shortly after the sonication and during the dip-coating process. The percent area coverage of the TiO$_2$ on the samples also increased from below 10% to above 40% as the number of dipping increased from 2 to 8, respectively. Based on the AFM image analysis, A100 coated samples had approximately 20%, 35%, and 40% TiO$_2$ area coverages in FIGS. 3A, 3B, and 3C, respectively (FIGS. 5A-5D). The RMS roughness of all three samples was between 90 nm and 100 nm. To achieve 50% TiO$_2$ area coverage, the number of dips was increased from 8 to 10 in a 250 mg/L solution (FIGS. 5A-5D). Based on this preliminary coating optimization, the test samples were prepared by dipping them 10 times in a 250 mg/L TiO$_2$ solution. The prepared samples maintained high optical transparency even after 10 rounds of coating in comparison to the uncoated samples (see FIG. 6).

The TiO$_2$ coated samples were tested for surface roughness and hydrophilicity, and the results are reported in Table 3. Roughness and hydrophilicity are two major factors that influence bacterial attachment because rough and hydrophobic surfaces are more susceptible to organic and bacterial adhesion compared to smooth and hydrophilic surfaces. The uncoated glass samples had RMS roughness below 3 nm, while the TiO$_2$ coated samples had RMS roughness of approximately their respective particle sizes. The hydrophilicity of the samples was measured by obtaining the water contact angle in the dark and after 45 minutes of UV irradiation. The contact angles of the uncoated glass samples were between 19° and 35° (35.7°±3.92°, 19.4°±4.5°, and 20.1°±5.05° for borosilicate glass, regular Gorilla® glass, and antimicrobial Gorilla® glass, respectively). In general, coating TiO$_2$ and its composites on the glass substrate decreased the contact angle (32% on average in comparison to the uncoated sample) and, in the presence of light, it decreased further (approximately 45% on average less than the illuminated uncoated sample), indicating an increase in hydrophilicity. The contact angle of the uncoated glasses, including the Gorilla® glasses, did not change appreciably after the UV irradiation. The greatest increase in hydrophilicity was observed for SWCNTs/A100, which achieved almost a 45% decrease in the contact angle after the UV exposure. The P25 samples showed the smallest contact angles and greatest hydrophilicity in comparison to the other surfaces. The lowest increase was observed for the uncoated and Gorilla glass samples, with slight decreases in contact angle after UV exposure. For the most part, the change in contact angle before and after UV irradiation was not notably different for the TiO$_2$ coated samples, with an average 28% decrease in contact angle, except for SWCNTs/A100 (44% decrease). This indicates that, in general, the effect of photoinduced superhydrophilicity (PSH) was significant, especially relative to the uncoated glass. PSH may be even greater with more complete coverage of TiO$_2$ on the substrate surface.

TABLE 3

Contact angle and surface roughness of the uncoated and TiO$_2$ coated samples

| Sample | Contact Angle (°) | Contact Angle after UV irradiation (°) | Surface roughness (nm) |
|---|---|---|---|
| Uncoated | 35.7 ± 3.92 | 32.4 ± 2.7 | 0.48 ± 0.23 |
| A100 | 24.0 ± 3.6 | 16.3 ± 2.2 | 90.11 ± 5.47 |
| A25 | 23.4 ± 0.5 | 18.8 ± 0.9 | 29.27 ± 10.45 |
| n-Ag/A100 | 25.2 ± 4.4 | 17.1 ± 1.7 | 80.43 ± 8.58 |
| n-Ag/A25 | 25.7 ± 3.7 | 16.0 ± 2.9 | 27.58 ± 8.10 |
| SWCNTs/A100 | 32.3 ± 5.4 | 18.0 ± 1.4 | 66.14 ± 3.51 |
| SWCNTs/A25 | 28.8 ± 2.6 | 21.7 ± 4.3 | 20.88 ± 8.26 |
| P25 | 18.5 ± 0.9 | 14.4 ± 1.8 | 41.24 ± 7.12 |
| Regular Gorilla® glass | 19.4 ± 4.5 | 18.6 ± 4.9 | 3.16 ± 1.83 |
| Antimicrobial Gorilla® glass | 20.1 ± 5.05 | 18.2 ± 3.7 | 0.83 ± 0.42 |

Cell Attachment and Viability Screening

Figure 4B:
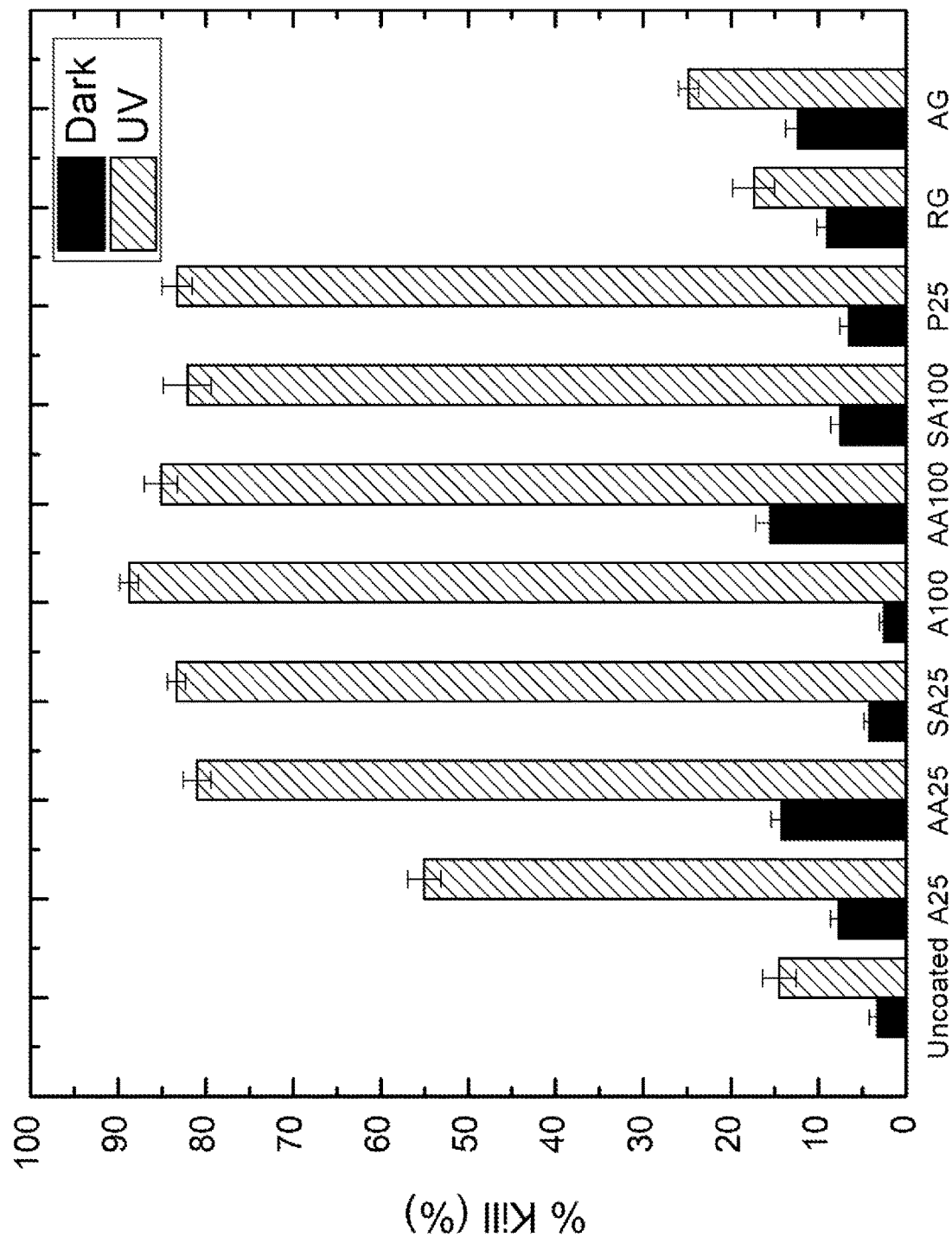
FIG. 4B shows % kill under dark and illuminated conditions. The regular and antimicrobial Gorilla® glass and SWCNTs and n-Ag doped A25 and A100 are abbreviated to RG, AG, SA25, AA25, SA100, and AA100, respectively. For each coating in the graph, the bar on the left is for dark conditions and the bar on the right is for UV conditions.

Confocal microscopy images of the attached bacterial cells on the uncoated and TiO$_2$ coated samples under two conditions (in the dark and after the UV irradiation) were obtained. For each type of sample, 30 images were taken and analyzed for bacterial attachment and % kill, as shown in FIGS. 4A and 4B, respectively. Here, the regular and antimicrobial Gorilla® glass, and the SWCNTs and n-Ag doped A25 and A100, are further abbreviated to RG, AG, SA25, AA25, SA100, and AA100, respectively. In FIG. 4A, the general trend shown reveals that there is no significant difference between the number of attached bacteria in the dark and after UV exposure, except for few samples, including A25, A100, AA100, and P25. In dark conditions, the uncoated sample had the lowest bacterial attachment due to its low roughness compared to the TiO$_2$ coated samples. The regular and antimicrobial Gorilla® glass also had relatively low bacterial attachment in the dark for the same reason. Nonetheless, the uncoated samples displayed minimal change in bacterial attachment after UV exposure. Among the test samples, the AA100 coated sample showed the best performance by having the lowest bacterial attachment and approximately 40% reduction relative to dark conditions after the UV irradiation. On the contrary, SA100 coated samples did not show a significant reduction in bacterial attachment, despite displaying the greatest increase in hydrophilicity. In the case of A25, the bacterial attachment increased under UV irradiation. Interestingly, P25 did not produce the lowest bacterial attachment. This suggests that, in most cases, the PSH effect of the TiO$_2$ coated samples was not great enough to overcome the increased surface roughness after 10 rounds of dip-coating.

In FIG. 4B, it is shown that the UV irradiation and TiO$_2$ based coating had a large influence on the % kill of the attached bacteria. Under dark conditions, n-Ag/TiO$_2$ coated samples (AA25 and AA100) displayed bactericidal activities close to those produced by UV exposure of the uncoated samples (≈15% kill), which are attributed to the silver nanoparticles and release of silver ions. The antimicrobial Gorilla® glass exhibited increased antibacterial activity from that of regular Gorilla® glass in dark conditions because it also contained an ionic silver component. Nonetheless, both AA25 (14.2% kill) and AA100 (15.5% kill) performed slightly better in killing *E. coli* than the antimicrobial Gorilla® glass (12.4% kill). Other TiO$_2$ coated samples had less than 10% kill in the dark, which was comparable to that of the uncoated samples in the dark because there is no light to activate the reaction at the TiO$_2$ surface. After the UV exposure, the % kill of the TiO$_2$ coated samples increased dramatically, exceeding 80% kill except for the A25 coated samples. These results are consistent with the methylene blue degradation test results in which A25 had the lowest degradation rate among the $TiO_2$ samples, but all the other $TiO_2$ materials showed similar extent and rates of decay. Compared to the $TiO_2$ coated samples, the uncoated samples had notably low post-UV % kill (<25%). For instance, the antimicrobial Gorilla® glass only killed around 25% of the attached bacteria, whereas the A100 coated samples killed approximately 90% of the attached bacteria. The high disinfection levels observed with most of the $TiO_2$ coated samples are due to the photocatalytic production of ROS that actively disrupt the cell membranes of the attached bacteria. On the contrary, the uncoated samples had low disinfection levels because of the absence of ROS and inadequate UV irradiation time for disinfection. Although the $TiO_2$-based coatings in this study exhibited similar degrees of antibacterial actions, the AA100 samples performed better overall in terms of reduction in bacterial attachment and antibacterial efficacy in the dark and under UV exposure.

Optical transparency was confirmed as follows. An AA100 sample showing >50% area coverage (see FIG. 5D) was measured for absorbance from 250 nm to 900 nm using a Shimadzu UV-Vis spectrophotometer (UV-2450). Absorbance of an uncoated borosilicate glass was also measured under the same condition for comparison. (See FIG. 7.) Absorbance data were obtained in triplicate and converted to % transmission. The average % transmission over the visible range was 99.93±0.034%, confirming that the sample is optically transparent to visible light.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the disclosure has been presented for purposes of illustration and of description. It is not intended to be exhaustive or to limit the disclosure to the precise form disclosed, and modifications and variations are possible in light of the above teachings or may be acquired from practice of the disclosure. The embodiments were chosen and described in order to explain the principles of the disclosure and as practical applications of the disclosure to enable one skilled in the art to utilize the disclosure in various embodiments and with various modifications as suited to the particular use contemplated. It is intended that the scope of the disclosure be defined by the claims appended hereto and their equivalents.

What is claimed is:

1. A method of reducing microbial attachment to a surface, the method comprising:
    illuminating a surface comprising a substrate and a coating on the substrate with ultraviolet light, wherein the coating consists of anatase titanium dioxide nanoparticles functionalized with silver nanoparticles and is optically transparent to visible light; and
    exposing the illuminated surface to microbes,
    wherein the coating exhibits a reduction in microbial attachment as compared to the coating absent the illumination.

2. The method of claim 1, wherein the reduction in microbial attachment is at least 30%.

3. The method of claim 1, wherein the reduction in microbial attachment is at least 40%.

4. The method of claim 1, wherein the coating exhibits an *Escherichia coli* ATCC 25922 attachment of no greater than 30 cells/1.5×10$^4$ µm$^2$ under illumination from a 1,000 W xenon arc lamp for 45 minutes.

5. The method of claim 1, wherein the reduction is an initial reduction and further comprising repeating the illumination and exposure steps at least one additional time, wherein the additional illumination step regenerates the coating to provide a subsequent reduction in microbial attachment after the additional exposure step.

6. The method of claim 5, wherein the subsequent reduction is the same as the initial reduction.

7. The method of claim 1, wherein the substrate is a display screen.

8. The method of claim 1, wherein the anatase titanium dioxide nanoparticles have an average particle size in the range from 20 nm to 120 nm and the silver nanoparticles have a smaller average particle size and no greater than 50 nm.

9. The method of claim 1, wherein the anatase titanium dioxide nanoparticles have an average particle size in the range from 80 nm to 110 nm and the silver nanoparticles have an average particle size in the range from 3 nm to 30 nm.

10. The method of claim 1, wherein the anatase titanium dioxide nanoparticles have an average particle size in the range from 80 nm to 110 nm and the silver nanoparticles have a smaller average particle size in the range from 3 nm to 30 nm, the coating has a mass ratio of silver to anatase titanium dioxide in a range of from 1:10 to 1:80, and the coating provides a percent area coverage on the substrate of at least 50% and a root-mean-square roughness of no greater than an average particle size of the anatase titanium dioxide nanoparticles.

11. A method of making an antimicrobial surface, the method comprising:
    applying a suspension of anatase titanium dioxide nanoparticles functionalized with silver nanoparticles to a substrate to form a coating thereon, wherein the coating is optically transparent to visible light and wherein the coating exhibits a reduction in microbial attachment under illumination with ultraviolet light as compared to the coating absent the illumination;
    wherein the coating consists of the anatase titanium dioxide nanoparticles functionalized with silver nanoparticles.

12. The method of claim 11, wherein the applying step is accomplished via dip-coating.

13. The method of claim 11, further comprising forming the suspension by exposing a mixture of anatase titanium dioxide nanoparticles and a silver salt in an organic solvent to ultraviolet light to reduce silver ions and form the anatase titanium dioxide nanoparticles functionalized with silver nanoparticles.

14. The method of claim 11, wherein the reduction in microbial attachment is at least 50%.

15. The method of claim 11, wherein the anatase titanium dioxide nanoparticles have an average particle size in the range from 80 nm to 110 nm and the silver nanoparticles have an average particle size in the range from 3 nm to 30 nm, the coating has a mass ratio of silver to anatase titanium dioxide in a range of from 1:10 to 1:80, and the coating provides a percent area coverage on the substrate of at least 50% and a root-mean-square roughness of no greater than an average particle size of the anatase titanium dioxide nanoparticles.

16. An antimicrobial surface comprising a substrate and a coating thereon, the coating consisting of anatase titanium dioxide nanoparticles functionalized with silver nanoparticles, wherein the coating is optically transparent to visible light and wherein the coating exhibits a reduction in microbial attachment under illumination with ultraviolet light as compared to the coating absent the illumination.

17. The surface of claim 16, wherein the reduction in microbial attachment is at least 50%.

18. The surface of claim 16, wherein the anatase titanium dioxide nanoparticles have an average particle size in the range from 80 nm to 110 nm and the silver nanoparticles have an average particle size in the range from 3 nm to 30 nm, the coating has a mass ratio of silver to anatase titanium dioxide in a range of from 1:10 to 1:80, and the coating provides a percent area coverage on the substrate of at least 50% and a root-mean-square roughness of no greater than an average particle size of the anatase titanium dioxide nanoparticles.

\* \* \* \* \*